US012396980B2

(12) United States Patent
Lindblad et al.

(10) Patent No.: US 12,396,980 B2
(45) Date of Patent: Aug. 26, 2025

(54) MELATONIN FOR PREVENTING AND TREATING RADIATION CYSTITIS

(71) Applicant: RepoCeuticals A/S, Høsholm (DK)

(72) Inventors: Lasse Lindblad, Ålsgårde (DK); Lars Otto Uttenthal, Madrid (ES)

(73) Assignee: REPOCEUTICALS A/S, Hørsholm (DK)

( * ) Notice: Subject to any disclaimer, the term of this patent is extended or adjusted under 35 U.S.C. 154(b) by 0 days.

(21) Appl. No.: 16/298,824

(22) Filed: Mar. 11, 2019

(65) Prior Publication Data

US 2020/0197367 A1  Jun. 25, 2020

Related U.S. Application Data

(63) Continuation of application No. 15/557,044, filed as application No. PCT/EP2016/055433 on Mar. 14, 2016, now abandoned.

(30) Foreign Application Priority Data

Mar. 13, 2015  (DK) .............. PA201570145

(51) Int. Cl.
| | |
|---|---|
| A61K 31/4045 | (2006.01) |
| A61K 9/08 | (2006.01) |
| A61K 31/122 | (2006.01) |
| A61K 31/167 | (2006.01) |
| A61K 31/355 | (2006.01) |
| A61K 31/375 | (2006.01) |
| A61K 31/385 | (2006.01) |
| A61K 47/20 | (2006.01) |

(52) U.S. Cl.
CPC ............ *A61K 31/4045* (2013.01); *A61K 9/08* (2013.01); *A61K 31/122* (2013.01); *A61K 31/167* (2013.01); *A61K 31/355* (2013.01); *A61K 31/375* (2013.01); *A61K 31/385* (2013.01); *A61K 47/20* (2013.01)

(58) Field of Classification Search
CPC ................................................ A61K 31/4045
See application file for complete search history.

(56) References Cited

U.S. PATENT DOCUMENTS

2008/0275015 A1  11/2008  Potter
2013/0251785 A1*  9/2013  Lander ............ A61K 9/0034
                                                        514/56

FOREIGN PATENT DOCUMENTS

| EP | 2702992 | 3/2014 | |
|---|---|---|---|
| WO | WO-0024387 A2 * | 5/2000 | ......... A61K 31/728 |
| WO | WO 02/41837 | 5/2002 | |
| WO | WO 2018/167273 A1 | 9/2018 | |

OTHER PUBLICATIONS

Cetinel et al., "The Ameliorating Effect of Melatonin on Protamine Sulfate Induced Bladder Injury and Its Relationship to Interstitial Cystitis", The Journal of Urology, 2003, 169: 1564-1568.
Maharaj et al., "Melatonin: New Places in Therapy", Biosci Rep, 2007, 27:299-320.
Payne et al., "Chemical- and radiation-induced hemorrhagic cystitis: current treatments and challenges", BJU Int., 2013, 112:885-897.
Sener et al., "Melatonin protects against ionizing radiation-induced oxidative damage in corpus cavernosum and urinary bladder in rats", Journal of Pineal Research, 2004, 37:241-246.
Yildirim et al., "Contribution of antioxidants to preventive effect of mesna in cyclophosphamide-induced hemorrhagic cystitis in rats", Cancer Chemotherapy Pharmacology, 2004, 54: 469-473.
Yildirim et al., "Contribution of antioxidants to preventive effect of mesna in cyclophosphamide-induced hemorrhagic cystitis in rats", Cancer Chemother Pharmacol, 2004, 54: 469-473.
Goksel Sener et al., "Melatonin protects against ionizing radiation-induced oxidative damage in corpus cavernosum and urinary bladder in rats", Journal of Pineal Research, 2004, 37: 241-246.
Li et al., "Postoperative external beam irradiation with and without brachytherapy in pelvic node-positive IB1-IIa2 cervical cancer patients: a retrospective clinical study", Radiation Oncology, 2015, 10: 189.
Vijayalaxmi et al., "Melatonin protects human blood lymphocytes from radiation-induced chromosome damage", Mutation Research, 1995, 346: 23-31.
Pranil et al., "Influence of pH, temperature, and light on the stability of melatonin in aqueous solutions and fruit juices", Heliyon, 2020, 6: e03648, 7 pages.

* cited by examiner

*Primary Examiner* — Yong S. Chong

(74) *Attorney, Agent, or Firm* — James S. Keddie; Bozicevic, Field & Francis LLP

(57) ABSTRACT

Compositions comprising melatonin and/or derivatives thereof are provided for topical administration to the epithelium of the urinary bladder by instillation into the bladder to protect against or treat bladder injury due to irradiation and/or cytotoxic agents.

11 Claims, No Drawings

MELATONIN FOR PREVENTING AND TREATING RADIATION CYSTITIS

CROSS-REFERENCE TO RELATED APPLICATIONS

This application is a continuation of U.S. application Ser. No. 15/557,044, which is a § 371 national phase of International Application No. PCT/EP2016/055433, filed on Mar. 14, 2016, which claims the benefit of Danish Application No. PA201570145, filed on Mar. 13, 2015, which applications are incorporated by reference herein.

FIELD OF INVENTION

The present invention provides compositions comprising melatonin and/or an antioxidant metabolite, derivative or analogue thereof as the essential ingredient for preventing and treating injury to the urinary bladder due to ionizing radiation by introducing the composition into the bladder. As such, it is particularly relevant to the fields of urological, prostatic, gynecological and colorectal oncology and radiotherapy, as well as surgery when this is part of a combined treatment with radiotherapy.

BACKGROUND OF THE INVENTION

Radiation Injury to the Urinary Bladder (Radiation Cystitis)

Radiation cystitis, in its acute and chronic manifestations, has been well reviewed by Muruve (2014), to whose article the following summary is indebted. Radiation cystitis is a complication of radiation therapy to pelvic tumors. The urinary bladder can be irradiated intentionally for the treatment of bladder cancer or incidentally for the treatment of other pelvic malignancies. Manifestations of radiation cystitis can range from minor, temporary voiding symptoms and painless, microscopic hematuria to more severe complications, such as gross hematuria, contracted, nonfunctional bladder, persistent incontinence, fistula formation, bladder necrosis, and death.

Tumors of the pelvic organs such as the prostate gland, urinary bladder, colon and rectum are common in men, constituting 42% of expected new cancer diagnoses in 2014. In women, cancer of the colon and rectum, bladder, and genital tract (uterus, ovary, and vagina/vulva) are expected to make up 22% of new cancer diagnoses in 2014. Radiation therapy is important for the treatment of these malignancies, creating a significant potential for the development of radiation injury to the urinary bladder. Therapeutic radiation may be delivered via various external sources. It may be applied directly to the tumor, such as in interstitial or intracavitary therapy (brachytherapy), or it can be delivered by external beam therapy.

Pathologic mechanisms: Radiation therapy works through the transfer of energy from ionizing radiation to molecules within tumor cells and related tissues. Radiation interacts with intracellular water and produces free radicals to an extent that exceeds the cells' intrinsic scavenging capabilities and can thus interfere with DNA synthesis, resulting in cell death. Cells that divide rapidly are most susceptible to radiation injury. Peak sensitivity to radiation is at the M and G2 phases of the cell reproductive cycle.

Radiation may also directly cause rapid cell death from mitotic arrest, point mutations in deoxyribonucleic acid (DNA), and cell membrane damage. Concomitant use of cytotoxic chemotherapeutic agents may work synergistically to increase the risk of developing bladder injury from radiation. Examples of cytotoxic agents that are known to cause tissue injury or exacerbate radiation injury are bleomycin, mitomycin C, bis-chloroethylnitrosourea (BCNU or carmustine), cyclophosphamide, busulfan, methotrexate, doxorubicin, gemcitabine, paclitaxel, docetaxel and carboplatin. Radiation can also cause vascular changes. Subendothelial proliferation, edema, and medial thickening may progressively deplete the blood supply to the irradiated tissue. Collagen deposition may also cause severe scarring and further blood-vessel obliteration, resulting in tissue hypoxia and necrosis. The fibrotic barriers left behind can also impair revascularization.

These features lead to mucosal ischemia and epithelial damage. In the bladder, this in turn may cause further submucosal fibrosis as the subepithelial tissues become exposed to the caustic effects of urine. Ulcer formation, radiation neuritis, and post-radiation fibrosis may cause the clinical findings of pain and discomfort.

Pathologic findings in radiated bladders can be grouped into early and late findings. Early findings are here defined as those occurring within 12 months after treatment, whereas late findings occur more than 12 months after treatment. Early findings include submucosal inflammation and fibrosis, perineural inflammation, surface ulceration, and epithelial atypia such as nuclear pleomorphism, hyperchromatism and granular cytoplasm, which may also be a late finding. Late findings include changes that are mainly fibrovascular and demonstrated by luminal occlusion, vascular ectasia, and necrosis of vessel walls. Cells with epithelial damage show cytoplasmic vacuolization and epithelial proliferation. Physiologically, these changes may produce clinical symptoms resulting from ischemia and fibrosis leading to loss of bladder muscle fibers and thus to dysfunctional voiding, and denervation hypersensitivity from ischemia causing abnormal neural stimulation of the bladder.

The rate of long-term complications depends on the volume and area of bladder affected, the trigone being more symptomatic than the bladder dome, the dose rate and daily fraction size, doses >2 Gy/fraction increasing the risk, and the total dose of irradiation received, the risk being higher with total doses >60 Gy.

Incidence: Because of the variations dosages and field size, and differences in the collection of data, the reported frequencies of radiation cystitis are very variable. Data are cited from Muruve (2014) and sub-references therein. For prostate cancer, the overall frequency of radiation cystitis 1 year after treatment is 9-21% (mean 14%). For lower grades of radiation cystitis according to the Radiation Therapy Oncology Group/European Organization for Research and Treatment of Cancer (RTOG/EORTC) scoring system (see below), the frequency may be as high as 65%. Equivalent figures for cervical cancer are 3-7% (mean 5%), and for 2-47% (mean 18%) for bladder cancer, with lower grades affecting up to 49%.

After treatment for bladder cancer, acute symptoms observed during treatment and lasting for less than 1 year are usually self-limiting and occur in 50-80% of patients, regardless of tumor type.

The RTOG grading scale of complications of bladder irradiation is as follows:

Grade 1—Any slight epithelial atrophy, microscopic hematuria, mild telangiectasia;

Grade 2—Any moderate frequency, generalized telangiectasia, intermittent macroscopic hematuria, intermittent incontinence;

Grade 3—Any severe frequency and urgency, severe telangiectasia, persistent incontinence, reduced bladder capacity (<150 ml), frequent hematuria;

Grade 4—Any necrosis, fistula, hemorrhagic cystitis, bladder capacity (<100 ml), refractory incontinence requiring catheter or surgical intervention;

Grade 5—Death.

This scale has been used in epidemiological surveys and as an aid to prognosis and clinical decision-making.

Current treatment of radiation cystitis is largely symptomatic. Frequency and urgency of micturition are treated with anticholinergic agents. Oral phenazopyridine, a urinary analgesic, may be used to provide symptomatic relief of persistent dysuria. Oral pentosan polysulfate sodium may be used to try to restore the bladder glycosaminoglycan layer, and oral pentoxifylline may be given to reduce blood viscosity and hence improve bladder oxygenation and reduce pain.

For macroscopic hematuria, oral conjugated estrogens may be given and a variety of agents may be instilled into the bladder. The antifibrinolytic agent aminocaproic acid may be instilled to promote hemostasis by inhibiting clot dissolution. Alum may be instilled to coagulate proteins and inhibit further bleeding. Formalin may be instilled as a sclerosing agent or applied endoscopically to bleeding points, both these procedures requiring general anesthesia. Similarly, ethoxysclerol may be injected endoscopically into bleeding areas.

For persistent failure of symptomatic treatment, hyperbaric oxygen therapy is tried. This can potentially reverse some aspects of radiation damage, e.g. by stimulating angiogenesis. However, significant fibrosis and ischemia cannot be reversed.

Prevention of radiation cystitis is in its infancy. Systemic (e.g. intramuscular) orgotein, copper-zinc superoxide dismutase of bovine origin, has been tried with variable success. However, this is a foreign protein which may provoke immune reactions on repeated use. Dimethyl sulfoxide (DMSO) has also been described as having a radioprotective effect, but human experience is sparse. DMSO did have some therapeutic effect on radiation cystitis in human patients (Shirley et al 1978). The use of systemically administered free-radical scavengers is an attempt to increase the radical scavenging capacity of the cells which are not intended to be injured by the radiotherapy. However, concerns have been raised that this could potentially decrease the effectiveness of anticancer therapy. So far, this concern has not been convincingly substantiated.

Medical need for the prevention and treatment of radiation cystitis: From the above description, it can be seen that there is clearly a need for a more effective medical prevention and treatment of radiation cystitis that is directed at the root cause of the pathology, the damage to healthy cells caused by the generation of intracellular free radicals as a direct and immediate effect of irradiation, and the persistence of an inflammatory and fibrotic response to the initial pathology.

SUMMARY OF THE INVENTION

The invention consists of providing pharmaceutical compositions comprising melatonin and/or an antioxidant metabolite, derivative or analogue thereof (individually referred to as the protective agent) to improve the prevention and treatment of radiation cystitis by the direct administration of the compositions to the bladder epithelium in the form of a solution or emulsion introduced into the bladder. The advantage of the invention is that the protective agent is delivered at high dose directly to the tissue for which protection from radiation damage is desired, while in cases other than bladder cancer there is no direct delivery to the tumor that is to be treated by radiotherapy. A further advantage will be that the directly applied melatonin will not be subject to the low bioavailability of melatonin given orally, which is subject to individually variable first-pass metabolism in the liver. The compositions are intended to be administered immediately or less than an hour before each dose of radiotherapy is given and at various other times during and after a course of radiotherapy.

Pharmaceutical compositions are also provided which comprise melatonin and/or an antioxidant metabolite, derivative or analogue thereof together with a pharmaceutically acceptable form of vitamin E and/or coenzyme Q10 and/or alpha-lipoic acid and/or vitamin C.

Accordingly, the pharmaceutical compositions comprise essentially:

A composition comprising melatonin and/or an antioxidant metabolite, derivative or analogue thereof formulated to be suitable for administration to the bladder epithelium as a solution, emulsion or suspension, for the prevention and treatment of radiation cystitis.

A composition according to that described above, comprising additionally a pharmaceutically acceptable form of vitamin E and/or coenzyme Q10 and/or alpha-lipoic acid vitamin C.

The invention fulfills the medical need for a preventive, pre-emptive and continuing treatment of the root intracellular cause of radiation injury to urinary bladder, for which current treatments are symptomatic or directed at post-hoc alleviation of longer-term pathological consequences.

In the following detailed description of the invention, details of the scope of the invention will be given, together with details of the practical performance of the invention.

DETAILED DESCRIPTION OF THE INVENTION

The present invention provides compositions comprising melatonin or an antioxidant metabolite, derivative or analogue thereof as the principal active substance to be instilled into the urinary bladder for the prevention and treatment of radiation cystitis. Radiation cystitis may be exacerbated by the concurrent use of cytotoxic chemotherapy, and the compositions are also intended for use to prevent and treat damage to the urinary bladder caused or exacerbated by cytotoxic agents. The invention also provides for compositions for the same purpose, which additionally comprise a pharmaceutically acceptable form or derivative or analogue of one or more of the substances vitamin E, coenzyme Q10, alpha-lipoic acid and vitamin C.

Active Ingredients

The principal active ingredient of the compositions of the invention is melatonin or an antioxidant metabolite, derivative or analogue thereof.

Melatonin

Melatonin (/V-acetyl-5-methoxytryptamine) is a hormone produced by the pineal gland in human beings and other mammals by enzymatic modification of the amino acid tryptophan. Melatonin is involved in maintaining the circadian rhythm of various biological functions, being secreted in hours of darkness and acting on high-affinity melatonin $G_i$-coupled transmembrane receptors MT1 and MT2, which are widely distributed in many cells and tissues of the body. At the same time melatonin acts at supraphysiological concentrations as a powerful antioxidant and free radical scavenger for ROS and reactive nitrogen species (Gomez-Moreno et al 2010). Melatonin can also activate cytoprotective antioxidative enzymes such as copper-zinc and manganese superoxide dismutases (CuZnSOD and MnSOD) and glutathione peroxidase (Rodriguez et al 2004). Melatonin also has anti-inflammatory effects to prevent the upregulation or cause the down-regulation of the expression of nuclear factor kappa B (N F-KB) and pro-inflammatory cytokines such as tumor necrosis factor alpha (TN F-a) and interleukin 1 beta (IL-1β).

Melatonin as an agent to protect against radiation injury: Because of melatonin's efficiency as a free radical scavenger, especially of hydroxyl radicals (Tan et al 1993) and ROS, it has been proposed as an agent to protect against radiation injury to cells and tissues. The protective effect of high dose systemic melatonin against the harmful effects of whole-body irradiation has been studied chiefly in rodents. Melatonin has typically been given at intravenous or intraperitoneal doses of 5 mg to 100 mg per kilogram of body weight and protective effects on DNA and nuclear morphology, as well as prolonged survival after lethal doses of irradiation have been observed. A protective effect of intraperitoneal melatonin against radiation-induced oxidative changes to the rat urinary bladder has been reported (Sener et al 2004). Melatonin has been demonstrated to protect against the adverse effects of all relevant wavelengths ionizing radiation from ultraviolet through x-rays to gamma rays. The results of such studies have been reviewed by Vijayalaxmi et al (2004). In human beings, a protective effect of prior oral melatonin dosage on the damage caused by subsequent ex vivo radiation exposure of lymphocytes has been observed (Vijayalaxmi et al 1996). However, controlled clinical trials of the protective effect of oral or systemic melatonin on radiation damage in patients undergoing radiotherapy are lacking.

The above experiments suggest that a major part of the protective effect of melatonin against radiation damage depends on the intracellular presence of melatonin at the time of radiation. This would be consistent with the near instantaneous intracellular production of free radicals as a result of radiation and their initiation of DNA and mitochondrial damage leading to cell death. As mentioned above, there has been some concern that pre-treatment with systemically administered melatonin might also diminish the effectiveness of radiotherapy to kill tumor cells. On the other hand, the effects of melatonin to activate cytoprotective enzymes and down-regulate pro-inflammatory cytokines points to a longer term effect that might contribute to protection against the later consequences of radiation cystitis.

Melatonin Metabolites, Derivatives and Analogues

Many chemical derivatives of melatonin, including breakdown products and natural metabolites of melatonin, retain the antioxidant and free-radical scavenging properties of the parent molecule. This makes melatonin a more effective antioxidant than other natural antioxidants such as vitamins C and E (cited by Reiter et al 2007). However, these vitamins show synergy with melatonin with respect to antioxidant activity. In non-hepatic tissues, the reaction of melatonin with two hydroxyl radicals yields the metabolite cyclic 3-hydroxymelatonin (C3-OHM), which undergoes further oxidation by two hydroxyl radicals to break the indole ring and form $/v^1$-acetyl-$/V^2$-formyl-5-methoxykynuramine (AFMK) (Tan et al 1993; Reiter et al 2007). C3-OHM is therefore also an effective antioxidant and hydroxyl radical scavenger. The reaction of melatonin with the hydroxyl radical precursor, hydrogen peroxide, similarly leads to production of AFMK. AFMK is also a reducing agent, capable of donating electrons to detoxify radical species, and has been shown to preserve the integrity DNA exposed to oxidizing agents. The action of aryl formamidase or catalase on AFMK produces $/v^1$-acetyl-5-methoxykynuramine (AMK), which is an even more effective scavenger of hydroxyl radicals and reactive nitrogen species, protecting proteins from oxidative destruction. In this process, 3-acetamidomethyl-6-methoxycinnolinone (AMMC) or 3-nitro-AMK (AMNK) are formed.

The liver is the principal site of the classically reported metabolic pathway for melatonin. This consists chiefly of 6-hydroxylation by the cytochromes P450 CYP1A1, CYP1A2, and CYP1B1 , and the formation of the minor metabolite /V-acetylserotonin by CYP2C19. The main product 6-hydroxymelatonin (6-OHM) is then conjugated at the hydroxyl group to form the 6-OHM glucuronide or 6-OHM sulfate. 6-OHM is an effective free radical scavenger in a variety of situations, but is also reported to show pro-oxidant effects in others. Its status as an antioxidant thus remains equivocal (Maharaj et al 2007).

/V-acetylserotonin (NAS) is not only the immediate biosynthetic precursor but also a minor metabolite of melatonin. Like 6-OHM, it is conjugated to form the glucuronide or sulfate. Its protective effect against oxidative damage in certain model systems is reportedly 5 to 20 times as strong as that of melatonin (Oxenkrug 2005).

Melatonin can also be chemically modified by introducing chemical groups at one or more of any of its constituent atoms susceptible of such modification or by introducing such groups in de novo synthesis of melatonin analogues or derivatives. Such modifications, which do not alter the fundamental indole structure of melatonin, are herein called derivatives. The fundamental indole structure of melatonin can also be modified by substituting other bicyclic aromatic structures. Such modifications are herein called analogues, which may also have different chemical side groups removed, introduced or modified. Many such analogues and derivatives have been prepared, but most of them have not been tested for their antioxidant or free-radical scavenging properties.

Natural Antioxidants That May Act in Synergy With Melatonin

A large number of natural antioxidant agents that have been used pharmaceutically may potentially act synergically with melatonin. These may have additive antioxidant effects, but only a few have been demonstrated to act synergically. Vitamins C and E have been cited in this context. A related but not identical property, which is less well assessed, is their efficiency as free radical scavengers and in conferring protection against the harmful effects of radiation and cytotoxic medication. Further natural antioxidants that come under consideration as conferring addition protective effect are alpha-lipoic acid and coenzyme Q10 (also known as ubidecarenone). Both are effective as free radical scavengers and their capacity to ameliorate radiation damage has been demonstrated in vitro and in animal models in which the substances have usually been given intraperitoneally or by dietary supplementation.

Antioxidant metabolites of melatonin: Of those described above, /v¹-acetyl-/V²-formyl-5-methoxykynuramine (AFMK), 6-hydroxymelatonin (6-OHM) and N-acetylserotonin (NAS) can be used in compositions of the invention. Cyclic 3-hydroxymelatonin (C3-OHM) and /v¹-acetyl-5-methoxykynuramine (AMK) are unstable and hence unsuitable for use in a pharmaceutical composition.

Antioxidant melatonin derivatives: The chemical structure of melatonin can be represented as in Figure (I), in which sites suitable for chemical modification by the substitution of different chemical groups have been indicated by R-i, $R_2$, R3, $R_4$, R5 and $R_6$. These numbers do not correspond to the conventional numbering of positions in the indole ring of melatonin.

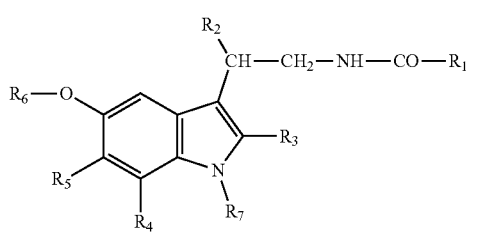

II

In native melatonin, $R_1$ and $R_6$ represent $CH_3$, while $R_2$, R3, $R_4$, R5 and $R_7$ represent H.

Antioxidant melatonin derivatives may comprise, as non-exclusive examples, those in which $R_1$ represents H, a linear or branched $C_1$-$C_4$ alkyl group or a $C_1$-$C_4$ alkoxy group, $R_2$ represents H or a $C_1$-$C_4$ alkyl group, $R_3$ represents H, a methyl group or a halogen atom, $R_4$ represents H or a halogen atom, $R_5$ represents H or a halogen atom, $R_6$ represents H or a linear or branched $C_1$-$C_4$ alkyl group, $R_7$ represents H, a linear or branched $C_1$-$C_4$ alkyl group, a —C(=0)-0—$R_a$ group or a —C(=0)—N(H)—$R_a$ group wherein $R_a$ is a linear or branched $C_1$-$C_4$ alkyl group, the —$CH_2$—NH—C(=O)—$R_1$ side chain is extended by duplicating, triplicating or quadruplicating the —$CH_2$— group, or pharmaceutically acceptable salts of such derivatives.

Synergically acting antioxidants: The present invention also provides compositions comprising melatonin or an antioxidant analogue or metabolite thereof together with a synergically acting antioxidant such as vitamin E, coenzyme Q10, alpha-lipoic acid or vitamin C as active substances. Said substances are herein referred to collectively as the active substances or ingredients. In their native forms, vitamin E is an oil, coenzyme Q10 is an almost water-insoluble solid of low melting point, and alpha-lipoic acid is a water-insoluble solid organic acid, while vitamin C is a solid organic acid.

These substances must be provided in forms that are appropriate for the pharmaceutical formulation used. For aqueous carriers, a water-soluble form of vitamin E is D-alpha-tocopheryl succinate. Coenzyme Q10 or a suitable antioxidant analogue or derivative thereof, non-limiting examples of which are coenzyme Q9, decylubiquinone and idebenone, may be rendered water-soluble by adsorption to a biologically acceptable carrier such as beta-cyclodextrin during the formulation process. Alpha lipoic acid R-(+)-alpha-lipoic acid, also called (R)-thioctic acid, can be used as its sodium salt, sodium thioctate, which is soluble in water to yield solutions of near-physiological pH. Similarly, a non-limiting example of an appropriate form of vitamin C is sodium ascorbate.

However, all the above active substances in their non-derivatized forms are readily soluble in dimethyl sulfoxide (DMSO), a solvent that can safely be instilled into the urinary bladder, and which has itself been used as a free-radical scavenging, antioxidant treatment for radiation cystitis (Shirley et al 1978).

Formulations

The pharmaceutical composition of the present invention may be in the form of a solution, emulsion or suspension, which may be introduced into the urinary bladder e.g. by instillation via a transurethral urinary catheter.

The formulation typically contains from 1 mg to 100 mg of melatonin or antioxidant metabolite, derivative or analogue thereof per milliliter of the composition. If other active ingredients are added, such as a pharmaceutically acceptable form of vitamin E and/or coenzyme Q10 and/or alpha-lipoic acid and/or vitamin C, they are added in an amount ranging from 25% to 200% by weight of the amount of melatonin or a metabolite, derivative or analogue thereof.

In the preferred embodiment, the formulation is a solution of the active ingredients in DMSO.

In another embodiment, the formulation is an aqueous solution or emulsion or suspension suitable for instillation into the bladder. A non-limiting example of such a formulation is a solution of a spray-dried powder prepared by mixing equal volumes of a solution of active ingredient in ethanol or DMSO and an aqueous solution of the sugar excipient, which may be lactose, mannitol or xylitol, and then spray-drying the ingredients to produce particles of median diameter less than 50 ∝η with over 90% by weight of particles being less than 100 ∝η in diameter. Small amounts, not exceeding 0.4% by weight, of biocompatible detergents such as sodium deoxycholate or lecithin may be added to the solution before spray-drying. Reconstitution of the spray-dried powder with water makes it possible to achieve aqueous solutions with concentrations of active ingredient of 2 mg/mL or more.

In yet another embodiment, the active ingredients are dissolved in another water-miscible, biologically compatible solvent, such as propylene glycol or one or more of several biocompatible solubilizing agents known to the skilled person.

Solutes to be added to the water in the dissolved pharmaceutical composition may include hydrochloric acid, sodium hydroxide and biocompatible buffering agents, non-limiting examples being sodium dihydrogen phosphate and disodium hydrogen phosphate, sodium carbonate and bicarbonate. Tonicity-adjusting agents, such as for example sodium chloride or calcium chloride, may also be added, as well as a suitable preservative such as methyl and/or propyl parahydroxybenzoate.

Formulations according to the present invention may comprise pharmaceutically acceptable carriers and excipients including microspheres, liposomes, micelles, microcapsules, nanoparticles or the like. In an aqueous suspension of liposomes containing melatonin, which is a relatively hydrophobic substance, the liposomes are unilamellar and their production is well known to the skilled person.

The stated formulation methods can also be applied to the melatonin metabolites, derivatives and analogues of the invention and to D-alpha-tocopheryl succinate, coenzyme Q10 or its analogues and derivatives. In the case of coenzyme Q10 or its analogues and derivatives, the substance is added to the mixture for spray drying in a water-soluble form complexed with a low-molecular weight dextrin, such as beta-cyclodextrin. Sodium ascorbate is water-soluble and presents no unusual formulation requirement.

Administration

Administration of an effective amount of the pharmaceutical composition is by topical application to the bladder epithelium by direct introduction into the bladder. In a preferred embodiment, this is performed by instillation via a transurethral urinary catheter.

Suitable catheters are hydrophilic, surface-coated catheters and the technique of clean, intermittent catheterization or clean, intermittent self-catheterization (CISC) is employed.

In particularly sensitive patients in which catheterization fails, direct injection into the bladder with a syringe can be employed.

The solution containing the active ingredients in DMSO is supplied in dark containers containing an effective single dose in a volume ranging from 10 mL to 50 ml, preferably 25 mL. Immediately before instillation the solution in DMSO is diluted with a volume of a physiologically compatible aqueous medium, which may be physiological saline (0.9% NaCl). The volume of aqueous medium used to dilute the DMSO solution may be an equal volume or a volume in the range of 30% to 300% of the volume of the DMSO solution. Aqueous solutions containing the active ingredients without DMSO are supplied in containers of an effective single dose in a volume of 20 mL to 100 mL, preferably 50 mL, for instillation without prior dilution.

The solution is instilled slowly to avoid spasm, and analgesic suppositories may be inserted prior to catheterization and instillation in particularly sensitive patients. After the instillation, the catheter is removed. The bladder is voided after the radiotherapy has been given.

If continuing treatment is given between radiotherapy sessions or after radiotherapy has been completed, the solution is left in the bladder for up to 4 hours or until the patient has to void the bladder.

Indications

1. Pelvic external beam radiotherapy for any condition requiring it, including conditions such as prostatic carcinoma, carcinoma of the rectum or anus, carcinoma of the bladder, cervical carcinoma and endometrial carcinoma.
2. Pelvic brachyradiotherapy for any condition requiring it, including conditions such as prostatic carcinoma, carcinoma of the rectum or anus, carcinoma of the bladder, cervical carcinoma and endometrial carcinoma.
3. A combination of 1. and 2.
4. Cystitis attributed to the use of cytotoxic medication.

Dose and Dosage Regimens

By "effective amount" of the pharmaceutical compositions of the present invention is meant a dose, which, when administered to a subject in need thereof, achieves a concentration which has a beneficial biological effect, i.e. by preventing or reducing radiation injury to the urinary bladder. Such an effective amount may be determined by physicians of ordinary skill in the art attending patients undergoing pelvic radiotherapy and/or brachyradiotherapy on appropriate clinical trial.

The effective amounts and dosages of the ingredients of the composition are not determined in relation to body weight or body surface area, because the treatment is local to the urinary bladder.

The effective amount of melatonin or an analogue, derivative or metabolite thereof for a single dose of intravesical administration may be from 1 mg to 500 mg, such as in the range of 10 mg to 300 mg, and especially in the range of 25 mg to 250 mg.

The effective amount of a pharmaceutically acceptable form of vitamin E and/or coenzyme Q10 and/or alpha-lipoic acid and/or vitamin C, in admixture with melatonin or a metabolite, derivative or analogue thereof, may be the same by weight as the amount of melatonin or a metabolite, derivative or analogue thereof, or in the range of 25% to 200% by weight of said amount.

The effective dose is preferably administered 15 minutes to 30 minutes before each dose of radiation and/or chemotherapy is given. Because melatonin may also have longer term anti-inflammatory effects that are not directly dependent on free radical scavenging, the effective dose may also be given up to twice daily between and after doses of radiation, and during and after chemotherapy, for a period of up to 12 months after the initiation of radiotherapy and/or chemotherapy. The daily dose may be given once a day or in divided or full effective doses twice daily, or even more, depending on practicability and tolerance, such as three times a day or four times a day. The total daily dose may thus be from one to four times the amount of a single effective dose.

Duration of dosing will typically range from 3 months to 12 months. A dosage regimen will typically comprise administering a dose prior to each session of radiotherapy and/or chemotherapy, with further doses being given thereafter on the same day and/or on intervening days, and dosing being continued after the cessation of radiotherapy and/or chemotherapy at the discretion of the attending physician.

A dose regimen may alternate between periods of administration of the pharmaceutical composition according to the present invention and periods without administration (a pause in treatment). A period with a pause of treatment in such a dose regime may last for 1 week to 2 weeks, or 2 weeks to 3 weeks, or 3 weeks to 1 month, or 1 month to two months, all at the discretion of the attending physician.

EXAMPLES

The following examples illustrate the clinical testing of the invention.

Example 1: Clinical Trial of the Effect of a Composition of the Invention on the Development of Radiation Cystitis A composition according to the present invention is tested for its efficacy in preventing radiation cystitis by means of a randomized, placebo-controlled, double-blind clinical trial on up to 50 adult patients that are to be treated with external radiotherapy to the pelvic region for cancer of a pelvic organ. After giving written, informed consent, the patients are taught to self-catheterize the urinary bladder with a hydrophilic surface-coated catheter through which the composition is self-administered, e.g. in a volume of 50 mL for a single standard dose. The patients are randomized to receive a standard dose of a composition of the present invention or a placebo composition without active ingredients 15-30 minutes before each fraction of radiotherapy is given. The clinician in charge of the trial may also determine that the standard dose should be repeated before retiring each night for the duration of the radiotherapy. The primary outcome is the effect on the RTOG score described above, supplemented with the EPIC (Expanded Prostate Index Composite) score for the urinary domain (Chang et al 2011). The RTOG and EPIC scores are determined for each patient immediately before starting radiotherapy and again after conclusion of the radiotherapy.

Example 2: Clinical Trial of the Effect of a Composition of the Invention to Alleviate Established Radiation Cystitis A composition according to the present invention is tested for its efficacy in alleviating established radiation cystitis by means of a randomized, placebo-controlled double-blind clinical trial on up to 50 adult patients that have been clinically and cystoscopically assessed to have established radiation cystitis. After giving written, informed consent, the patients are taught to self-catheterize the urinary bladder with a hydrophilic surface-coated catheter through which the composition is self-administered, e.g. in a volume of 50 mL for a single standard dose. The patients in the treatment arm self-administer a standard dose of a composition of the present invention before retiring each night for 28 consecutive nights. The patients in the control arm do the same with a placebo composition without active ingredients. All patients continue with their conventional symptomatic treatment. The primary outcome is the effect on the RTOG score described above, supplemented with the EPIC (Expanded Prostate Index Composite) score for the urinary domain (Chang et al 2011). The RTOG and EPIC scores are determined for each patient immediately before starting treatment and again after conclusion of the treatment period. The secondary outcome will consist of a blinded assessment of the findings on any cystoscopy performed after the end of treatment.

REFERENCES

Chang P, Szymanski K M, Dunn R L, Chipman J J, Litwin M S, Nguyen P L, Sweeney C J, Cook R, Wagner A A, DeWolf W C, Bubley G J, Funches R, Aronovitz J A, Wei J T, Sanda M G (2011) Expanded prostate cancer index composite for clinical practice: development and validation of a practical health related quality of life instrument for use in the routine clinical care of patients with prostate cancer. J Urol 186:865-872.

Gomez-Moreno G, Guardia J, Ferrera M J, Cutando A, Reiter R J (2010) Melatonin in diseases of the oral cavity. Oral Dis 16:242-247.

Maharaj D S, Glass B D, Daya S (2007) Melatonin: new places in therapy. Biosci Rep 27:299-320.

Muruve N A (2014) Radiation Cystitis. Medscape, CME & Education, last updated 9 Nov. 2014. http://emedicine.medscape.com/article/2055124-overview.

Oxenkrug G (2005) Antioxidant effects of N-acetylserotonin: possible mechanisms and clinical implications. Ann N Y Acad Sci 1053:334-347.

Reiter R J, Tan D X, Terron M P, Flores L J, Czarnocki Z (2007) Melatonin and its metabolites: new findings regarding their production and their radical scavenging actions. Acta Biochim Pol 54:1-9.

Rodriguez C, Mayo J C, Sainz R M, Antolin I, Herrera F, Martin V, Reiter R J (2004) Regulation of antioxidant enzymes: a significant role for melatonin. J Pineal Res 36:1-9.

Sener G, Atasoy B M, Ersoy Y, Arbak S, Sengoz M, Yegen B C (2004) Melatonin protects against ionizing radiation-induced oxidative damage in corpus cavernosum and urinary bladder in rats. J Pineal Res 37:241-246.

Shirley S W, Stewart B H, Mirelman S (1978) Dimethyl sulfoxide in treatment of inflammatory genitourinary disorders. Urology 11:215-220.

Tan D X, Chen L D, Poeggeler B, Manchester L C, Reiter R J (1993) Melatonin: a potent, endogenous hydroxyl radical scavenger. Endocrine J 1:57-60.

Vijayalaxmi, Reiter R J, Herman T S, Meltz M L (1996) Melatonin and radioprotection from genetic damage: in vivo/in vitro studies with human volunteers. Mutat Res 371:221-228.

Vijayalaxmi, Reiter R J, Tan D X, Herman T S, Thomas C R Jr (2004) Melatonin as a radioprotective agent: a review. Int J Radiat Oncol Biol Phys 59:639-653.

The invention claimed is:

1. A method for reducing urinary bladder injury selected from radiation cystitis caused by irradiation by pelvic external beam radiotherapy and/or irradiation by pelvic brachyradiotherapy, comprising:
   (a) administering a composition consisting of melatonin, dimethyl sulfoxide (DMSO), water and optionally sodium chloride directly into the urinary bladder of a subject; and
   (b) administering a treatment to the subject, wherein the treatment comprises: radiation treatment to the subject by pelvic external beam radiotherapy and/or pelvic brachyradiotherapy;
   wherein administering step (a) is done within one hour before administering step (b) and at intervals after step (b).

2. The method of claim 1, wherein the radiation cystitis is exacerbated by additional treatment of the subject with a dose of one or more cytotoxic agents.

3. The method of claim 1, wherein the melatonin is formulated as a solution in dimethyl sulfoxide (DMSO) and diluted in an aqueous medium prior to use.

4. The method of claim 3, wherein the concentration of dimethyl sulfoxide (DMSO) in the solution is between 100 parts of dimethyl sulfoxide to 300 parts of water by volume and 100 parts of dimethyl sulfoxide to 30 parts of water by volume.

5. The method of claim 1, wherein the composition is administered 1, 2, 3, or 4 times per day.

6. The method of claim 1, wherein the composition is administered over a period of up to 3 months.

7. The method of claim 6, wherein the composition is administered over a period of up to 12 months.

8. The method of claim 1, wherein a single standard dose of melatonin is 1 mg to 500 mg.

9. The method of claim 8, wherein the daily dose of the composition is from one to four times the single standard dose.

10. The method of claim 1, wherein the composition is administered directly into the urinary bladder within 30 minutes before the treatment of (b) is administered to the subject, and at intervals thereafter.

11. The method of claim 1, wherein the composition consists of 10 mL to 50 mL of DMSO, 25 mg to 250 mg of melatonin, water, and optionally sodium chloride.

* * * * *